(12) United States Patent
Polander et al.

(10) Patent No.: US 8,921,553 B2
(45) Date of Patent: Dec. 30, 2014

(54) STANNYL DERIVATIVES OF NAPHTHALENE DIIMIDES AND RELATED COMPOSITIONS AND METHODS

(75) Inventors: Lauren E. Polander, San Diego, CA (US); Seth R. Marder, Atlanta, GA (US)

(73) Assignee: Georgia Tech Research-Corporation, Atlanta, GA (US)

( * ) Notice: Subject to any disclaimer, the term of this patent is extended or adjusted under 35 U.S.C. 154(b) by 0 days.

(21) Appl. No.: 14/110,996

(22) PCT Filed: Apr. 13, 2012

(86) PCT No.: PCT/US2012/033598
§ 371 (c)(1),
(2), (4) Date: Feb. 10, 2014

(87) PCT Pub. No.: WO2012/142466
PCT Pub. Date: Oct. 18, 2012

(65) Prior Publication Data
US 2014/0213789 A1 Jul. 31, 2014

Related U.S. Application Data

(60) Provisional application No. 61/591,767, filed on Jan. 27, 2012, provisional application No. 61/579,608, filed on Dec. 22, 2011, provisional application No. 61/475,888, filed on Apr. 15, 2011.

(51) Int. Cl.
*C07F 7/22* (2006.01)
*H01L 51/50* (2006.01)
*H01L 51/00* (2006.01)
*C07D 471/06* (2006.01)
*C07D 519/00* (2006.01)

(52) U.S. Cl.
CPC .......... *H01L 51/0067* (2013.01); *C07D 471/06* (2013.01); *C07D 519/00* (2013.01)
USPC ........................................... 546/10; 313/504

(58) Field of Classification Search
USPC ...................................... 546/10, 66; 313/504
See application file for complete search history.

(56) References Cited

U.S. PATENT DOCUMENTS

| | | |
|---|---|---|
| 2010/0252112 A1 | 10/2010 | Watson |
| 2010/0261901 A1 | 10/2010 | Rybtchinski et al. |
| 2011/0046341 A1 | 2/2011 | Ie et al. |

FOREIGN PATENT DOCUMENTS

| | | |
|---|---|---|
| EP | 1736476 A1 | 12/2006 |
| EP | 2 251 335 A1 | 11/2010 |
| WO | 2009098253 A1 | 8/2009 |
| WO | 2009144205 A1 | 12/2009 |
| WO | 2009144302 A1 | 12/2009 |

OTHER PUBLICATIONS

Shanks, David; Preus, Soren; Qvortrup, Katrine; Hassenkam, Tue; Nielsen, Mogens Brondsted; Kilsa, Kristine—Excitation energy transfer in novel acetylenic perylene diimide scaffolds—New Journal of Chemistry (2009), 33(3), 507-516.

Vosch, Tom; Fron, Eduard; Hotta, Jun-Ichi; Deres, Ania; Uji-I, Hiroshi; Idrissi, Abdenacer; Yang, Jaesung; Kim, Dongho; Puhl, Larissa; Haeuseler, Andreas; Mullen, Klaus; De Schryver, Frans C.; Sliwa, Michel; Hofkens, Johan—Synthesis, ensemble, and single molecule characterization of a diphenyl-acetylene linked perylenediimide trimer—Journal of Physical Chemistry C (2009), 113(27), 11773-11782.

Chen, Zhihua; Zheng, Yan; Yan, He; Facchetti, Antonio—Naphthalenedicarboximide- vs Perylenedicarboximide-Based Copolymers. Synthesis and Semiconducting Properties in Bottom-Gate N-Channel Organic Transistors—Journal of the American Chemical Society (2009), 131(1), 8-9.

Qifan Yan and Dahui Zhao—Conjugated Dimeric and Trimeric Perylenediimide Oligomers—Organic Letters 2009 vol. 11, No. 15 3426-3429.

Durban, Matthew M.; Kazarinoff, Peter D.; Luscombe, Christine K.—Synthesis and Characterization of Thiophene-Containing Naphthalene Diimide n-Type Copolymers for OFET Applications—Macromolecules (2010), 43 (15), 6348-6352.

Yonggang Zhen, Wan Yue, Yan Li, Wei Jiang, Simone Di Motta, Eugenio Di Donato, Fabrizia Negri, Song Ye and Zhaohui Wang—Chiral Nano-ribbons Based on Doubly-linked Oligo-perylene Bisimides—Chem. Commun., 2010,46, 6078-6080 (Supporting information).

Zachary E. X. Dance et al: "Direct Observation of the Preference of Hole Transfer over Electron Transfer for Radical Ion Pair Recombination in Donor-Bridge-Acceptor Molecules", Journal of the American Chemical Society, vol. 130, No. 3, Jan. 1, 2008, pp. 830-832.

Zachary E. X. Dance et al: Supporting Information for "Direct Observation of the Preference of Hole Transfer over Electron Transfer for Radical Ion Pair Recombination in Donor-Bridge-Acceptor Molecules", J. Am. Chem. Soc., vol. 130, Jan. 1, 2008, pp. S1-S18.

*Primary Examiner* — Charanjit Aulakh

(57) ABSTRACT

Naphthalene diimide (NDI) compounds can be functionalized with tin reagent to provide a useful, versatile synthetic tool. One embodiment provides, for example, a composition comprising at least one NDI compound comprising at least one stannyl substituent bonded to the naphthalene moiety of the NDI compound. Applications include organic electronic devices including OLED, OPV, OFET, and sensing devices.

19 Claims, No Drawings

STANNYL DERIVATIVES OF NAPHTHALENE DIIMIDES AND RELATED COMPOSITIONS AND METHODS

This application is a U.S. national phase entry under 35 U.S.C. §371 of International Application No. PCT/US2012/033598, filed on Apr. 13, 2012, which claims priority to U.S. Provisional Application No. 61/475,888, filed on Apr. 15, 2011; U.S. Provisional Application No. 61/579,608, filed on Dec. 22, 2011; and U.S. Provisional Application No. 61/591,767, filed on Jan. 27, 2012, the entirety of all of which is being incorporated herein by reference for all purposes.

BACKGROUND

Organic electronics is an important area for commercial development including, for example, advanced transistors, displays, lighting, photovoltaic, and sensing devices. The broad diversity of organic compounds and materials provides advantages for organic electronics. In but one example of the versatile chemistry and material science available for organic electronics, tetracarboxylic diimide derivatives of rylenes, particularly of napthalene and perylene (NDIs and PDIs, respectively), represent one of the most extensively studied classes of functional materials in the field of organic electronics. The thermal, chemical, and photochemical stability as well as their high electron affinities and charge-carrier mobilities render these materials attractive for applications in organic field-effect transistors (OFETs) and organic photovoltaic cells (OPVs). They have also been widely used as acceptors in transient absorption studies of photoinduced electron-transfer, again due to their redox potentials, and to the stability and distinctive absorption spectra of the corresponding radical anions.

The N,N'-substituents of PDIs and NDIs generally only have minimal influence on the optical and electronic properties of isolated molecules, although they can be used to control solubility, aggregation, and intermolecular packing in the solid-state. In contrast, core substitution of these species typically has a much more significant effect on the redox potentials (enabling, in some cases, the electron affinities to be brought within a range in which air-stable OFET operation can be achieved) and optical spectra of these species. Moreover, core substitution can be used as a means of constructing more elaborate architectures such as conjugated oligomers or polymers and donor or acceptor functionalized products.

Functionalized NDIs are most effectively obtained through the selective bromination of naphthalene-1,4:5,8-tetracarboxylic dianhydride (NDA) with dibromoisocyanuric acid (DBI) in concentrated sulfuric acid or oleum, followed by imidization with the primary amine of choice in refluxing acetic acid. NDA can also be brominated using $Br_2$ in concentrated sulfuric acid or oleum. The brominated NDI can then serve as an intermediate for further functionalization through either nucleophilic substitution to afford amino, thiol or alkoxy substituted derivatives, or through palladium-catalyzed coupling reactions to yield cyano, phenyl, alkynyl and thienyl functionalized products. However, the range of conjugated species that can be obtained by palladium-catalyzed methods is determined by the availability of appropriate candidate coupling partners. In particular, metallated reagents such as stannanes can be difficult to obtain for electron-poor (acceptor) building blocks.

Additionally, monobrominated NDI, which is useful for a full range of NDI derived compounds, generally can only be obtained by manipulating the equivalents of brominating reagents and/or by manipulating reaction conditions; however, a difficult to separate mixture of non-brominated, monobrominated, and dibrominated results, which makes large scale production impractical.

Accordingly, both mono- and di-metallated NDI species would be valuable building blocks for new types of conjugated NDI derivatives in which acceptor groups are directly conjugated to the NDI core.

SUMMARY

Embodiments described herein include compositions and compounds, as well as methods of making, methods of using, inks, and devices comprising these compositions and compounds.

One embodiment provides a naphthalene diimide (NDI) compound comprising at least one stannyl substituent bonded to the naphthalene core of the NDI compound.

Another embodiment provides the compound which is represented by the structure:

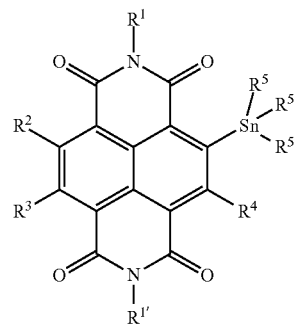

wherein $R^1$ and $R^{1'}$ are independently selected from a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups;

$R^2$, $R^3$, and $R^4$ are independently selected from hydrogen, halide, or a $C_1$-$C_{30}$ organic group independently selected from cyano, normal, branched, or cyclic alkyl, fluoroalkyl, aryl, heteroaryl, alkyl-aryl, and alkyl-heteroaryl groups, optionally substituted with one or more fluoro, cyano, alkyl, alkoxy groups, or one or more of $R^2$, $R^3$, and $R^4$ are optionally $Sn(R^5)_3$; and $R^5$ is an alkyl or aryl group.

In another embodiment, $R^2$, and $R^4$ are independently selected from hydrogen, fluoro and cyano; and $R^3$ is independently selected from hydrogen, halide, or a $C_1$-$C_{30}$ organic group independently selected from cyano, normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups and $Sn(R^5)_3$ wherein $R^5$ is as previously defined.

Another embodiment provides a compound which is a mono-stannyl NDI compound represented by the structure:

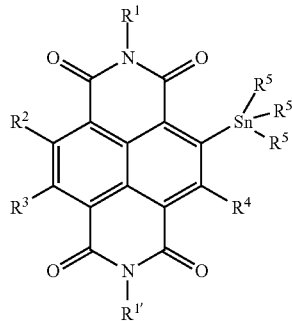

wherein
a) $R^1$ and $R^{1'}$ are independently selected from a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups,
b) $R^2$, $R^3$, and $R^4$ are independently selected from hydrogen, halide, or a $C_1$-$C_{30}$ organic group independently selected from cyano, normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups; and
c) $R^5$ is an alkyl or aryl group.

Another embodiment provides compounds as described herein but which exclude one or more mono-stannyl NDI compounds represented by the structure:

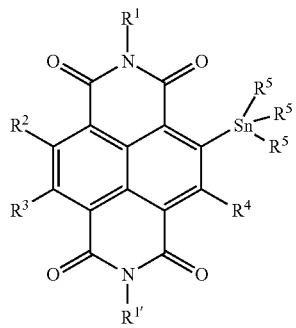

wherein
d) $R^1$ and $R^{1'}$ are independently selected from a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups,
e) $R^2$, $R^3$, and $R^4$ are independently selected from hydrogen, halide, or a $C_1$-$C_{30}$ organic group independently selected from cyano, normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups; and
f) $R^5$ is an alkyl or aryl group.

Another embodiment provides the compound which is a bis-stannyl NDI compound represented by the structure:

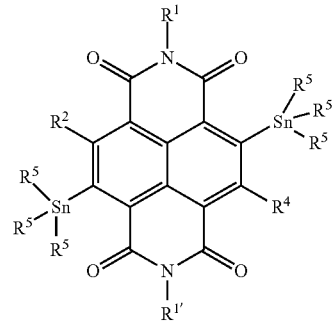

wherein
a) $R^1$ and $R^{1'}$ are independently selected from a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups,
b) $R^2$ and $R^4$ are independently selected from hydrogen, halide, or a $C_1$-$C_{30}$ organic group independently selected from cyano, normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups; and
c) $R^5$ is an alkyl or aryl group.

Another embodiment provides a composition comprising at least one naphthalene diimide (NDI) compound as defined in various embodiments described herein.

An embodiment for a method comprises a method comprising: reacting at least one first naphthalene diimide (NDI) precursor compound with at least one tin reagent to form at least one first NDI reaction product compound comprising at least one stannyl substituent bonded to the naphthalene core of the NDI compound.

In one embodiment, the tin reagent is an organotin reagent.

In another embodiment, the tin reagent comprises one or more of a hexaalkyl ditin reagent, or a hexaaryl ditin reagent.

In another embodiment, the tin reagent is not a halogenated tin reagent.

In another embodiment, in the reacting step, only one NDI precursor compound is reacted with the at least one tin reagent.

In another embodiment, the first NDI reaction product compound comprises one or two stannyl substituents.

In another embodiment, the first NDI reaction product comprises the structure:

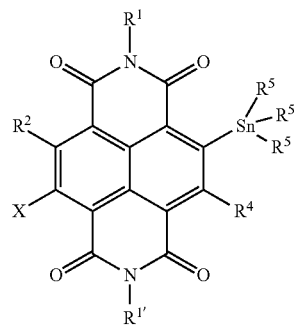

wherein X is H, R³ or a stannyl substituent Sn(R⁵)₃; wherein each R¹, R¹', R², R³, R⁴ and R⁵ are as previously defined.

In another embodiment, the first NDI reaction product comprises a mixture of the following structures:

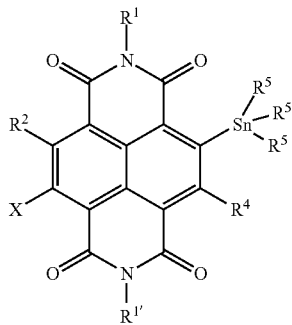

wherein X is H or R³;
and:

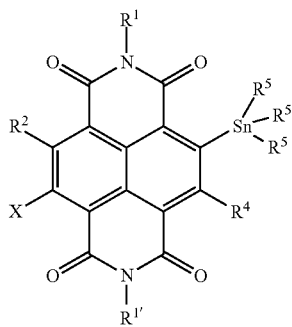

wherein X is Sn(R⁵)₃.

In another embodiment, the reacting step is carried out in the presence of at least one metal catalyst.

Another embodiment further comprises the separation of the stannyl NDI reaction products via chromatography.

Another embodiment provides a method, said method being a method for making the compounds as described herein or the compositions as described herein, said method comprising the steps of:

(a) providing or obtaining a monomeric naphthalene diimide precursor compound represented by the structure:

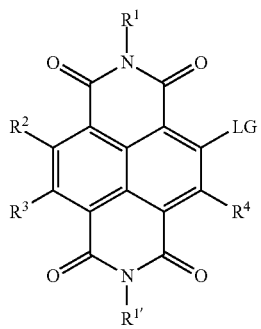

wherein LG is a halogen;

(b) reacting the monomeric naphthalene diimide precursor compound with a compound having the structure (R⁵)₃Sn—Sn(R⁵)₃, in the presence of a catalyst, wherein R⁵ is an alkyl or aryl group, to form at least some of the naphthalene diimide organotin compound, wherein R¹ and R¹' are previously defined, R², R³, and R⁴ are independently selected from hydrogen, halide, or a $C_1$-$C_{30}$ organic group independently selected from cyano, normal, branched, or cyclic alkyl, fluoroalkyl, aryl, heteroaryl, alkyl-aryl, and alkyl-heteroaryl groups, optionally substituted with one or more fluoro, cyano, alkyl, alkoxy groups.

Another embodiment provides for use of the organotin compounds as described herein or of the compositions as described herein or compounds or compositions made by the methods described herein, wherein the use is to form an oligomer or polymer.

Another embodiment is use of the oligomer of polymer formed as described herein as a semiconducting oligomer or polymer in an organic electronic device, including, for example, OLED, OPV, OFET, or sensing device.

One embodiment provides a composition comprising at least one naphthalene diimide (NDI) compound comprising at least one stannyl substituent bonded to the naphthalene moiety of the NDI compound, wherein in one embodiment, the compound has one stannyl substituent. In another embodiment, the compound has two stannyl substituents.

In one embodiment, the stannyl substituent is —SnR'₃ wherein the R' groups, independently, are alkyl or aryl.

In one embodiment, the NDI compound comprises at least one NDI moiety. In another embodiment, the NDI compound comprises at least two NDI moieties.

In one embodiment, the molecular weight of the compound is about 2,000 g/mol or less. In another embodiment, the molecular weight of the compound is about 1,000 g/mol or less. In another embodiment, the molecular weight of the compound is about 750 g/mol or less.

One embodiment provides for naphthalene diimide organotin compounds having the structure (I):

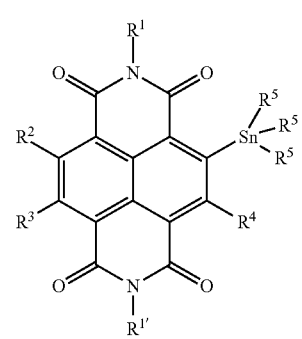

(I)

wherein R¹ and R¹' are independently selected from a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups; R², R³, and R⁴ are independently selected from hydrogen, halide, or a $C_1$-$C_{30}$ organic group independently selected from cyano, normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups or one or more of R², R³, and R⁴ are optionally Sn (R⁵)₃; and R⁵ is an alkyl or aryl group.

In one embodiment, R¹ and R¹' are independently a $C_1$-$C_{30}$ normal or branched alkyl or fluoroalkyl group. In another embodiment, R², R³, and R⁴ are independently selected from hydrogen, halide, or a $C_1$-$C_{30}$ organic group independently selected from cyano, normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups. In another embodiment, $R^2$, $R^3$, and $R^4$ are independently selected from hydrogen, fluoro and cyano. In another embodiment, $R^5$ is a $C_1$-$C_{12}$ alkyl group.

Another embodiment provides for naphthalene diimide organotin compounds having the structure (I'):

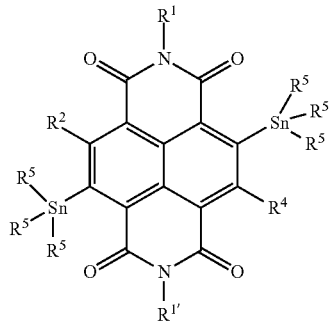

(I')

wherein $R^1$ and $R^{1'}$ are independently selected from a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups; $R^2$ and $R^4$ are independently selected from hydrogen, halide, or a $C_1$-$C_{30}$ organic group independently selected from cyano, normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups.

Another embodiment provides for naphthalene diimide organotin compounds having the structure (II):

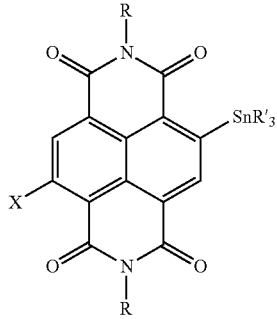

(II)

wherein X is H or a stannyl substituent; wherein each R is independently a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups; and wherein each of the R' moieties is independently an alkyl or aryl moiety. In one embodiment, each R is independently an optionally substituted $C_1$-$C_{30}$ alkyl moiety and each of the R' moieties is independently a $C_1$-$C_{20}$ alkyl moiety.

Another embodiment provides for naphthalene diimide organotin compounds having the structure (III):

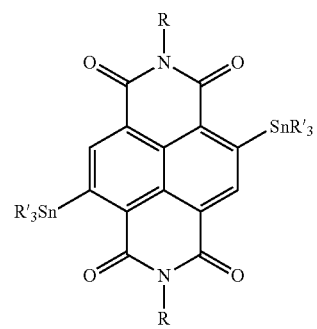

(III)

wherein each R is independently a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups; and wherein each of the R' moieties is independently an alkyl or aryl moiety. In one embodiment, each R is independently an optionally substituted $C_1$-$C_{30}$ alkyl moiety and each of the R' moieties is independently a $C_1$-$C_{20}$ alkyl moiety.

Another embodiment provides for naphthalene diimide organotin compounds having the structure (IV):

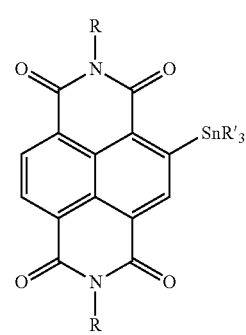

(IV)

wherein each R is independently a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups; and wherein each of the R' moieties is independently an alkyl or aryl moiety. In one embodiment, each R is independently an optionally substituted $C_1$-$C_{30}$ alkyl moiety and each of the R' moieties is independently a $C_1$-$C_{20}$ alkyl moiety.

Another embodiment provides a method for making the compounds of these embodiments, comprising the steps of:

(a) providing or obtaining a monomeric naphthalene diimide compound having the structure (V):

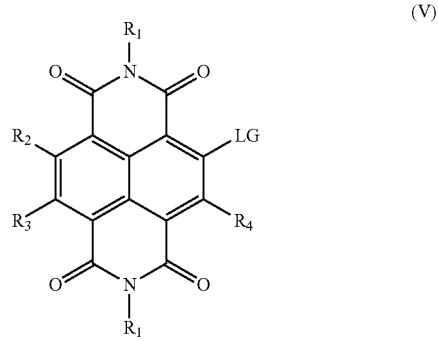

wherein $R^1$, $R^{1'}$ are independently selected from a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups; $R^2$, $R^3$, and $R^4$ are independently selected from hydrogen, halide, or a $C_1$-$C_{30}$ organic group independently selected from cyano, normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups; and LG is a halogen; and (b) reacting the monomeric naphthalene diimide compound with a compound having the structure $(R^7)_3Sn$—$Sn(R^7)_3$, in the presence of a catalyst, wherein $R^7$ is an alkyl or aryl group, to form at least some of the naphthalene diimide organotin compound. In another embodiment, $R_3$ of the monomeric naphthalene diimide compound of Step(a) is also LG.

Another embodiment provides for a method comprising: reacting at least one first naphthalene diimide (NDI) precursor compound with at least one tin reagent to form at least one first NDI compound comprising at least one stannyl substituent bonded to the naphthalene moiety of the NDI compound.

Another embodiment provides that the tin reagent is an organotin reagent. In one embodiment, the tin reagent is a ditin reagent. In one embodiment, the tin reagent is an alkyltin reagent. In one embodiment, the tin reagent is a hexabutylditin reagent. In one embodiment, the tin reagent is not a halogenated tin reagent.

In one embodiment, in the reacting step, only the one NDI precursor compound is reacted with the at least one tin reagent.

In one embodiment, in the reacting step, a mixture of two different NDI precursor compounds is reacted with the at least one tin reagent to form the at least one first NDI reaction product compound and also at least one second different NDI reaction product compound, wherein each of the first and second NDI reaction product compounds comprise at least one stannyl substituent bonded to the naphthalene moiety of the first and second NDI compounds.

In one embodiment, the first naphthalene diimide (NDI) precursor compound has zero, one, or two halogen moieties. In one embodiment, the first naphthalene diimide (NDI) precursor compound has one or two halogen moieties.

In one embodiment, the first NDI reaction product compound comprises one stannyl substituent and the second NDI reaction product compound comprises two stannyl substituents.

In one embodiment, the reacting step produces a mixture of the first and second different NDI reaction product compounds and the mixture is subjected to a separation procedure to separate the first and second NDI reaction product compounds.

In one embodiment, the first NDI compound is represented by a compound selected from Formulas (I)-(IV).

In one embodiment, the reacting step is carried out in the presence of at least one metal catalyst. In one embodiment, the reacting step is carried out in the presence of at least one palladium catalyst. In one embodiment, the first NDI reaction product compound has a molecular weight of about 2,000 or less.

Applicants have unexpectedly discovered a simple and efficient method for making naphthalene diimide organotin compounds comprising at least one stannyl substituent bonded to the naphthalene core of the NDI compound. Naphthalene diimide organotin compounds, now unexpectedly available as synthetic intermediates in view of Applicants new method for making them, can be readily coupled with functionalized precursors of a wide variety of electron withdrawing hAr heterocycles, such as heteroaryl dibromides or diiodides, to give new and previously unknown NDI-hAr-NDI oligomers wherein hAr is an electron withdrawing heterocycle. Such compounds can provide unexpectedly superior performing and ambient stable electron transport semiconductors.

At least one advantage for at least one embodiment is that a wide variety of new compounds and materials can be made or, alternatively, existing compounds and materials can be made more easily from the NDI-organotin compounds embodied herein. In particular, for at least one embodiment, the important Stille coupling reaction can be used more expansively for the NDI system to expand the variety of organic compounds and materials that can be made. This allows one to "tune" properties such as the ionization potential, oxidation potential, electron affinity, reduction potential, optical absorption, and fluorescence of the compound or material for a particular application so it can function well with other components.

DETAILED DESCRIPTION

Introduction

All references cited herein are incorporated by reference in their entirety.

Priority U.S. provisional application 61/475,888 filed Apr. 15, 2011 to Polander et al. is hereby incorporated by reference in its entirety including NDI-Sn compounds and methods of making NDI-Sn compounds. Also incorporated are the aryl and heteroaryl structures and working examples, including Figures. This application also provides more background information about the advantages and long-felt need associated with the presently claimed inventions. In some embodiments described herein, the NDI-Sn compounds and methods of making same which are described in the priority 61/475,888 provisional are excluded.

Also incorporated by reference in their entirety are priority U.S. provisional application 61/579,608 filed Dec. 22, 2011 and priority U.S. provisional application 61/591,767 filed Jan. 27, 2012.

The PhD thesis by Lauren Polander, 2011, "Organic Charge-Transport Materials Based on Oligothiophene and Napthalene Diimide: Towards Ambipolar and n-Channel Organic Field-Effect Transistors," provides additional information about the presently claimed inventions.

Important synthetic methods which can be used as appropriate herein to prepare compounds are generally described in *March's Advanced Organic Chemistry*, 6th Ed., 2007.

As used herein, "halo" or "halogen" or even "halide" can refer to fluoro, chloro, bromo, and iodo.

As used herein, "alkyl" can refer to a straight-chain, branched, or cyclic saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), and the like. In various embodiments, an alkyl group can have 1 to 30 carbon atoms, for example, 1-20 carbon atoms (i.e., $C_1$-$C_{20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted with 1-5 $R^1$ groups and $R^1$ is as defined herein.

As used herein, "haloalkyl" can refer to an alkyl group having one or more halogen substituents. At various embodiments, a haloalkyl group can have 1 to 20 carbon atoms, for example, 1 to 10 carbon atoms (i.e., $C_1$-$C_{10}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., perfluoroalkyl groups such as $CF_3$ and $C_2F_5$), are included within the definition of "haloalkyl."

As used herein, "alkoxy" can refer to —O-alkyl group. Examples of alkoxy groups include, but are not limited to, methoxy, ethoxy, propoxy (e.g., n-propoxy and isopropoxy), t-butoxy groups, and the like. The alkyl group in the —O-alkyl group can be substituted with 1-5 $R^1$ groups and $R^1$ is as defined herein.

As used herein, "heteroatom" can refer to an atom of any element other than carbon or hydrogen and includes, for example, nitrogen, oxygen, silicon, sulfur, phosphorus, and selenium.

As used herein, "heteroaryl" can refer to an aromatic monocyclic ring system containing at least one ring heteroatom selected from oxygen (O), nitrogen (N), sulfur (S), silicon (Si), and selenium (Se), or a polycyclic ring system wherein at least one of the rings present in the ring system is aromatic and contains at least one ring heteroatom. A heteroaryl group, as a whole, can have, for example, from 5 to 16 ring atoms and contain 1-5 ring heteroatoms (i.e., 5-16 membered heteroaryl group). In some embodiments, heteroaryl groups can be substituted with one or more terminal $R^1$ groups, where $R^1$ is as defined herein. Both substituted and unsubstituted heteroaryl groups described herein can comprise between 1-30, or 1-20 carbon atoms, including the $R^1$ substituents.

As used herein, "aryl" can refer to a broad variety of unsaturated cyclic groups which can provide conjugation and delocalization and can be fused and can be optionally substituted, as known in the art. Aryl groups with $C_6$ to $C_{40}$ or $C_6$ to $C_{30}$ in carbon number can be used, for example.

NDI-Sn Compositions

One embodiment provides, for example, a composition comprising at least one naphthalene diimide (NDI) compound comprising at least one stannyl substituent bonded to the naphthalene moiety of the NDI compound.

"Naphthalene diimide" or "naphthalene tetracarboxylic diimide" (NDI) compounds, derivatives, and materials are known in the art. See, for example, US Patent Publications 2011/0269967; 2011/0269966; 2011/0269265; 2011/0266529; 2011/0266523; 2011/0183462; 2011/0180784; 2011/0120558; 2011/0079773; 2010/0326527; and 2008/0021220. Other examples can be found in, for example, Hu et al., *Chem. Mater.*, 2011, 23, 1204-1215 ("core-expanded naphthalene diimides"); Wei et. al., *Macromol. Chem. Phys.*, 2009, 210, 769-775 ("naphthalene bisimides" or NBI); Jones et al., *Chem. Mater.*, 2007, 19, 11, 2703-2705; and Durban et al., *Macromolecules*, 2010, 43, 6348-6352; Guo et al., *Organic Letters*, 2008, 10, 23, 5333-5336 ("naphthalene bisimides"); Roger et al., *J. Org. Chem.*, 2007, 72, 8070-8075; Thalaker et al., *J. Org. Chem.*, 2006, 71, 8098-8105; Oh et al., *Adv. Funct. Mater.*, 2010, 20, 2148-2156; Suraru et al., *Synthesis*, 2009, 11, 1841-1845; Polander et al., *Chem. Mater.*, 2011, 23, 3408-3410; Yan et al., *Nature, Feb.* 5, 2009, 457, 679-686; Chopin et al., *J. Mater. Chem.*, 2007, 4139-4146; Bhosale et al., *New J. Chem.*, 2009, 33, 2409-2413; and Chen et al., *J. Am. Chem. Soc.*, 2009, 131, 8-9. In the present application, "NDI" and "NBI" are deemed equivalent. The core NDI structure can be called 1,4:5,8-napthalenetetracarboxylic acid diimide.

One representation of an NDI structure is as follows, showing the core naphthalene group and the two imide groups:

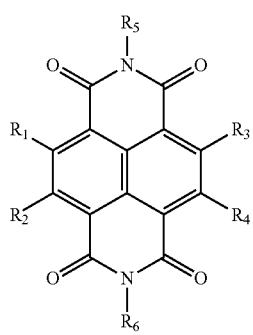

(NDI)

Herein, at least one of the substituents $R_1$, $R_2$, $R_3$, and/or $R_4$ can be functionalized to be a tin (or stannyl) group wherein the tin atom is directly covalently bonded to the naphthalene core. The identity of the two groups, $R_5$ and $R_6$ bonded to the imide, independently of each other are not particularly limited to the extent that the compounds can be synthesized. In one embodiment, the $R_5$ and $R_6$ groups are the same groups. The $R_5$ and $R_6$ bonded to the imide can be a broad range of organic groups. One example of the $R_5$ and $R_6$ group alkyl, including n-alkyl or branched alkyl, including for example, hexyl. Cyclic alkyl structures can be also used. The $R_5$ and $R_6$ groups can be optionally substituted with groups such as, for example, halide, cyano, alkyl, and/or alkoxy.

NDI compounds can be prepared from precursor compounds including, for example, naphthalene anhydride (NDA).

The naphthalene moiety in the NDI can be substituted on one or both of the carbocyclic aromatic rings comprising the naphthalene moiety. Four substitution sites are possible at the 2, 3, 6, and 7 positions of the NDI so there can be one, two, three, or four substituents. In addition, the one or both nitrogens of the imide groups in NDI can be also substituted. Substitution can promote solubility.

The naphthalene moiety in the NDI can be substituted on one or both of the carbocyclic aromatic rings comprising the naphthalene moiety with at least one stannyl substituent. The stannyl substituent can be represented by —$SnR'_3$. For example, the compound can have one stannyl substituent, or it can have two stannyl substituents.

In one embodiment, the NDI compound comprises at least one NDI moiety, whereas in another embodiment, the NDI compound comprises at least two NDI moieties, or at least three NDI moieties. Hence, for example, oligomers of NDI can be derivatized with one or more stannyl moieties.

In one embodiment, the molecular weight of the NDI-Sn compound is about 2,000 g/mol or less, or about 1,000 g/mol or less, or about 750 g/mol or less.

In one embodiment, the Applicants have unexpectedly discovered a ready and practical method for making naphthalene diimide organotin compounds (NDI-tin compounds) represented by the structure (I):

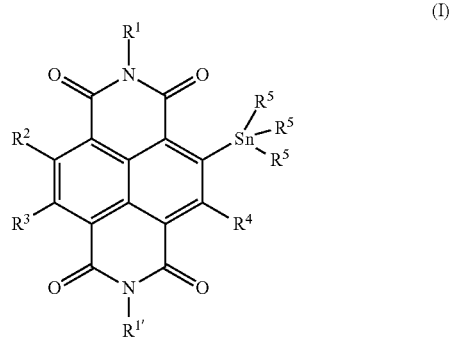

wherein $R^1$ and $R^{1'}$ are independently selected from a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups; $R^2$, $R^3$, and $R^4$ are independently selected from hydrogen, halide, or a $C_1$-$C_{30}$ organic group independently selected from cyano, normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups or one or more of $R^2$, $R^3$, and $R^4$ are optionally $Sn(R^5)_3$; and $R^5$ is an alkyl or aryl group. In one embodiment, $R^2$, $R^3$, and $R^4$ are independently selected from hydrogen, halide, or a $C_1$-$C_{30}$ organic group independently selected from cyano, normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups. In another embodiment, $R^2$, $R^3$, and $R^4$ are independently selected from hydrogen, fluoro and cyano. In another embodiment, $R^5$ is a $C_1$-$C_{12}$ alkyl group.

In another embodiment, the NDI-tin compound is represented by the structure (I'):

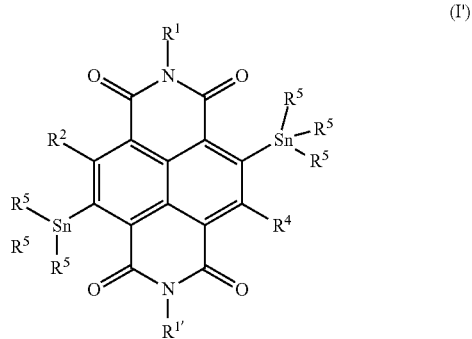

wherein $R^1$ and $R^{1'}$ are independently selected from a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups; $R^2$ and $R^4$ are independently selected from hydrogen, halide, or a $C_1$-$C_{30}$ organic group independently selected from cyano, normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups.

Such novel NDI-organotin compounds are highly useful as the "nucleophilic" component in well known palladium-catalyzed coupling reactions for making novel NDI-hAr oligomers, wherein hAr is an electron withdrawing heteroaryl group. There are a few examples in the art (see for example WO 2009/144205 and WO 2009/144302) to make PDI oligomers coupled to electron rich hAr groups, by coupling an electron withdrawing PDI bromide with an electron rich and nucleophilic organotin hAr precursor compound. But such coupling reactions typically fail if an electron withdrawing hAr group is employed. No starting NDI organotin compounds have (to Applicants' knowledge) been previously reported, so as to enable an "inverse" coupling method for the synthesis of NDI-hAr-NDI compounds with electron withdrawn hAr substituents.

Applicants' unexpected discovery (further described herein) of a method for synthesizing the novel NDI-organotin precursor compounds enables use of "inverted" coupling reactions for the synthesis of NDI-hAr-NDI oligomers having electron withdrawn hAr heteroaryl bridging groups, a class of NDI oligomer compounds with lower lying LUMOs (low lying LUMOs have been correlated in the art with improved air and water stability). Additionally, other useful compounds can be synthesized through coupling the NDI organotin compounds embodied herein, though known reactions, such as one or more Stillie reactions.

In some embodiments, $R^1$ and $R^{1'}$ are independently a $C_1$-$C_{30}$ normal or branched alkyl or fluoroalkyl group. In some embodiments, $R^2$, $R^3$, and $R^4$ are independently selected from hydrogen, fluoro and cyano. In many embodiments, $R^5$ is a $C_1$-$C_{12}$ alkyl group.

While NDI compounds are a preferred embodiment herein, higher rylene compounds such as PDI and related perylene compounds can be also functionalized with tin substituents and reacted to form additional compounds for use in, for example, organic electronic devices. Rylene compounds and moieties are known in the art. See, for example, Zhan et al., Adv. Mater., 2011, 23, 268-284. Besides NDI and PDI, other known rylene compounds include TDI, QDI, 5DI, and HDI, for example.

In one embodiment, the NDI compound is represented by the structure (II):

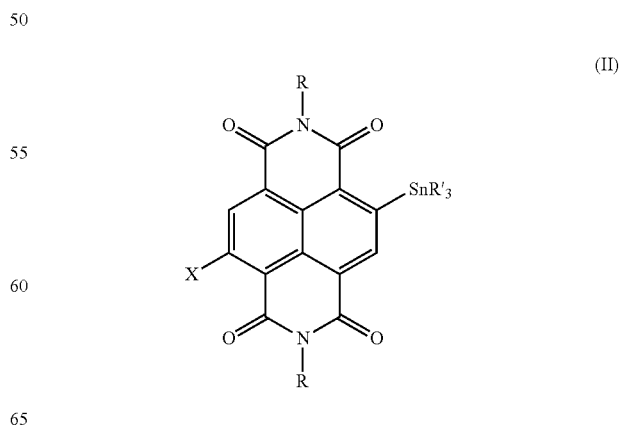

wherein X is H or a stannyl substituent; wherein each R is independently a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups; and wherein each of the R' moieties is independently an alkyl or aryl moiety. In another embodiment, each R is independently an optionally substituted $C_1$-$C_{30}$ alkyl moiety and each of the R' moieties is independently a $C_1$-$C_{20}$ alkyl moiety.

In another embodiment, the compound is represented by the structure (III):

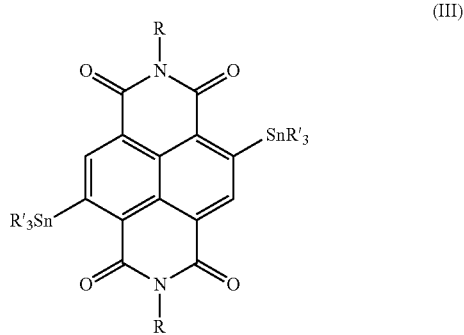

wherein each R is independently a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups; and wherein each of the R' moieties is independently an alkyl or aryl moiety. In another embodiment, each R is independently an optionally substituted $C_1$-$C_{30}$ alkyl and each of the R' moieties is independently a $C_1$-$C_{20}$ alkyl moiety.

In another embodiment, the compound is represented by the structure (IV):

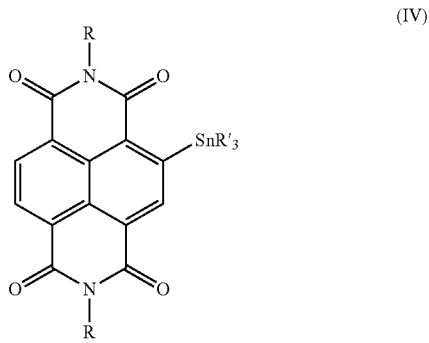

wherein each R is independently a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups; and wherein each of the R' moieties is independently an alkyl or aryl moiety. In another embodiment, each R is independently an optionally substituted $C_1$-$C_{30}$ alkyl and each of the R' moieties is independently a $C_1$-$C_{20}$ alkyl moiety.

Methods of Making NDI-Sn Compounds

Also described herein are methods of making the compounds described supra. For example, another embodiment provides for a method comprising: reacting at least one first naphthalene diimide (NDI) precursor compound with at least one tin reagent to form at least one first NDI compound comprising at least one stannyl substituent bonded to the naphthalene moiety of the NDI compound. Precursor compounds are described further below.

Tin reagents and organotin reagents are known in the art. For example, the tin reagent can be an alkyltin or aryltin reagent and preferably, an alkyltin reagent. The tin reagent can provide the tin moiety in the NDI compounds described supra, including formulas I, II, III and IV. The tin reagent can comprise two tin atoms per molecule (a "ditin" compound) such as, for example, $R'_3Sn$—$SnR'_3$ wherein R' is independently alkyl or aryl, and preferably alkyl. In one embodiment, the R' alkyl group are independently selected from a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups. The R' alkyl group can be, for example, a $C_1$-$C_{20}$ alkyl group including, for example, methyl or butyl (including n-butyl). In one example, the tin reagent is a hexabutylditin reagent.

In one embodiment, the tin reagent is not a halogen tin reagent. For example, tin reagents are known which can be represented by X—$SnR'_3$, wherein X is a halogen. However, such reagents can be excluded.

For one embodiment, in the reacting step, only one NDI precursor compound is reacted with the at least one tin reagent.

However, mixtures of different NDI precursor compounds can be subjected to reaction with tin reagent, and this use of mixtures can provide important advantages. In another embodiment, in the reacting step, a mixture of two different NDI precursor compounds is reacted with the at least one tin reagent to form the at least one first NDI reaction product compound and also at least one second different NDI reaction product compound, wherein each of the first and second NDI compounds comprise at least one stannyl substituent bonded to the naphthalene moiety of the first and second NDI compounds.

In one embodiment, for example, the first NDI compound comprises one stannyl substituent and the second NDI compound comprises two stannyl substituents.

In one embodiment, the reacting step produces a mixture of the first and second different NDI reaction product compounds and the mixture is subjected to a separation procedure to separate the first and second NDI reaction product compounds (e.g. chromatography).

In these reactions, as described in supra, the first NDI compound can be represented by a compound of Formulas (I)-(IV).

In addition, the below Scheme A illustrates a synthetic method starting from NDA precursor.

Scheme A

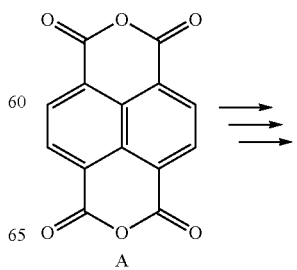

A

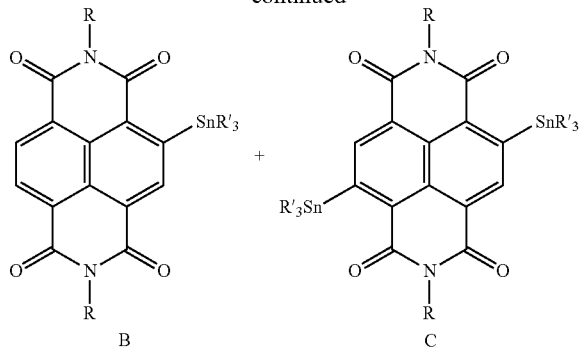

In Scheme A, the three arrows can represent, schematically, reaction steps which are needed to form the desired target: (i) halogenation of one or both of the naphthalene phenyl rings in compound A to allow introduction of the tin substituents to the naphthalene core, (ii) conversion of the two anhydride moieties in compound A (NDA) to the imide, and (iii) introduction of the tin moiety to the phenyl ring (replacing the halogen or halogens introduced in (i)). Starting from a single precursor compound A, the two tin reaction products, B and C, can be produced as a mixture and then separated by methods known in the art, such as chromatography as illustrated in the Working Examples, below. In Scheme A, the imide R and tin R' groups in B and C can be as described above, independently of each other. Purification steps can be carried out after any or each of the three steps (i), (ii), and (iii), including only after step (iii). Compounds B and C can be further substituted as described in Formulas (I)-(IV), and the compound A can, in some instances, contain corresponding substitution.

In additional embodiments, NDI-organotin compounds can be made by a method comprising the steps of (a) providing or obtaining a monomeric naphthalene diimide compound substituted with a leaving group LG, and represented by the structure (V);

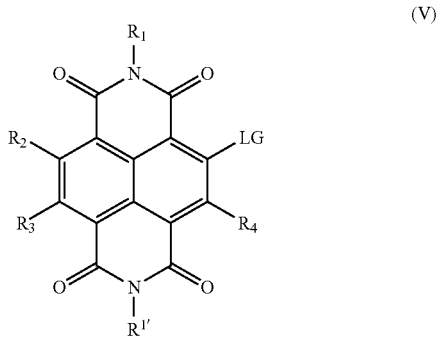

wherein $R^1$, $R^{1'}$ are independently selected from a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups; $R^2$, $R^3$, and $R^4$ are independently selected from hydrogen, halide, or a $C_1$-$C_{30}$ organic group independently selected from cyano, normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups; and LG is a halogen, such as Br or I; and (b) reacting the monomeric naphthalene diimide compound with a compound having the structure $(R^5)_3Sn$—$Sn(R^5)_3$, in the presence of a catalyst (typically soluble palladium compounds, such as the Stille coupling catalysts, e.g. $Pd_2(dba)_3$ and $P(o-tol)_3$ ligand), and wherein $R^5$ is an alkyl or aryl group, to form at least some of the naphthalene diimide organotin compounds. In another embodiment, $R^3$ of the monomeric naphthalene diimide compound of Step(a) is also LG.

This method for making isolatable quantities of the naphthalene diimide organotin compounds is unexpected. Without wishing to be bound by theory, it was expected that under such "Stille Coupling" conditions, the naphthalene diimide organotin compounds would be formed as a reaction intermediate, but would cross couple in-situ in a "Stille Coupling" with another molecule of the leaving-group substituted NDI, to generate an NDI-NDI dimer with directly coupled NDI groups. Unexpectedly, (especially in view of differing results with related perylenediimide compounds) the anticipated "dimerization" coupling reaction of bromide substituted NDI compounds did not proceed at a significant rate, but as a result the NDI organotin compounds can be isolated in good yield and used as synthetic intermediates to make other NDI-based materials. The nucleophilic NDI organotin compounds isolated from these unexpected reactions can however be readily coupled (in the presence of various appropriate palladium coupling catalysts well known to those of ordinary skill in the art) with other (less sterically hindered) bromide-substituted heteroaryl compounds, even if the brominated heteroaryl compounds are highly electron withdrawing, and enable the practical synthesis of NDI-hAr-NDI oligomers with electron withdrawn hAr bridging groups or other compounds, such as those described herein.

For introducing the tin substitutents, the reacting step can be carried out under reaction conditions known in the art and illustrated by the working examples herein. For example, purification, temperature, pressure, atmosphere, solvent, reaction time, catalyst, and other reaction parameters can be controlled for a particular synthesis. Reaction temperature can be, for example, 50° C. to 150° C. and reflux conditions can be used. Reaction time can be, for example, 3 h to 72 h. One or more organic solvents can be used such as an aromatic solvent like toluene. The catalyst materials can be introduced in one or more than one steps. Reaction yields can be, for example, at least 10%, at least 25%, or at least 50%.

Again, while methods related to NDI compounds are a preferred embodiment herein, higher rylene compounds such as PDI and related perylene compounds can be also functionalized with tin substituents and reacted to form additional compounds for use in, for example, organic electronic devices. Rylene compounds and moieties are known in the art. See, for example, Zhan et al., *Adv. Mater.*, 2011, 23, 268-284. Besides NDI and PDI, other known rylene compounds include TDI, QDI, 5DI, and HDI, for example.

Use of Stannylated Compounds

As disclosed above, the NDI-organotin compounds of the present invention are highly useful as "nucleophilic" components in well known palladium catalyzed coupling reactions, which afford access to a number of different types of compounds, which can be utilized as a semiconducting oligomer or polymer in an organic electronic device such as, for example, an OLED, OPV, OFET, or sensing device.

The following compounds are representative compounds that can be accessed utilizing the NDI-organotin compounds embodied herein. For example, certain compounds of this invention can be further reacted to form NDI-hAr-NDI oligomers of the generic structure:

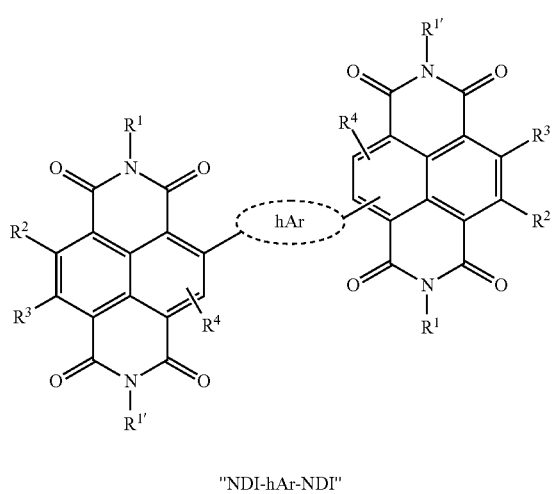

"NDI-hAr-NDI"

wherein hAr is a heteroaryl that bridges the two NDI group and the NDI compounds are substituted as defined in Formulas (I)-(IV). See, for example, U.S. provisional application 61/475,888 filed Apr. 15, 2011 to Polander et al. which is cited above and incorporated by reference. See also U.S. provisional application 61/591,767 filed Jan. 27, 2012 cited above.

If needed, these compounds can be further manipulated to achieve the resulting compound for use as a semiconducting oligomer or polymer in an OLED, OPV, OFET, or sensing device.

WORKING EXAMPLES

1. Materials and General Methods

Materials.

Starting materials were reagent grade and were used without further purification unless otherwise indicated. Solvents were dried by passing through columns of activated alumina (toluene, $CH_2Cl_2$), by distillation from Na/benzophenone (THF), or were obtained as anhydrous grade from Acros Organics. For reference, N,N'-Di(n-hexyl)naphthalene-1,4,5,8-bis(dicarboximide), 9, was synthesized according to the literature: (1) Rademacher, A.; Märkle, S.; Langhals, H. *Chem. Ber.* 1982, 115, 2927. (2) G. Hamilton, D.; Prodi, L.; Feeder, N.; K. M. Sanders, J. *J. Chem. Soc., Perkin Trans. 1* 1999, 1057. (3) Reczek, J. J.; Villazor, K. R.; Lynch, V.; Swager, T. M.; Iverson, B. L. *J. Am. Chem. Soc.* 2006, 128, 7995.

Hexabutyltin was obtained from Sigma-Aldrich.

Characterization.

Chromatographic separations were performed using standard flash column chromatography methods using silica gel purchased from Sorbent Technologies (60 Å, 32-63 μm). $^1$H and $^{13}$C{$^1$H} NMR spectra were obtained on a Bruker AMX 400 MHz Spectrometer with chemical shifts referenced using the $^1$H resonance of residual $CHCl_3$ or the $^{13}$C resonance of $CDCl_3$ unless otherwise indicated. Mass spectra were recorded on a Applied Biosystems 4700 Proteomics Analyzer by the Georgia Tech Mass Spectrometry Facility. Elemental analyses were performed by Atlantic Microlabs.

2. Synthetic Details

Example 1

Preparation of Compounds 1, 2

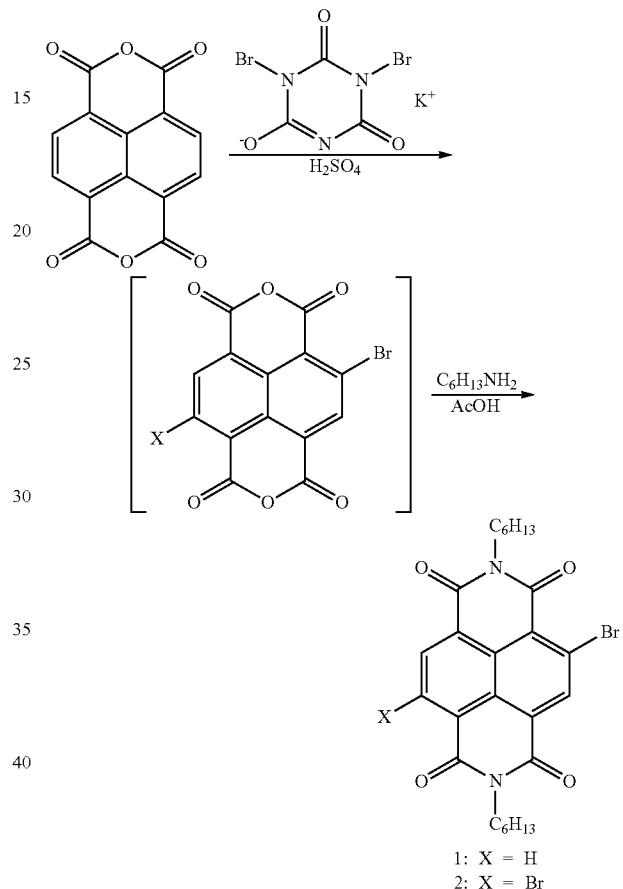

1: X = H
2: X = Br

A solution of naphthalene-1,4,5,8-tetracarboxydianhydride (10.0 g, 59.5 mmol) in concentrated sulfuric acid (600 mL) was heated to 85° C. After 30 min, potassium dibromoisocyanurate (19.3 g, 59.5 mmol) was added portionwise and the mixture was allowed to stir at 85° C. for 20 h. The mixture was poured into ice water (1.5 L) and allowed to stir for 2 h, while allowing to warm to room temperature. The resulting yellow precipitate was collected by filtration, washed with methanol, and dried under vacuum (16.6 g). The yellow solid was transferred to a flask with glacial acetic acid (600 mL) and n-hexylamine (19.4 g, 0.191 mol). The reaction mixture was refluxed for 20 min, allowed to cool overnight, and poured into methanol (1.5 L). The resulting precipitate was collected by filtration, washed with methanol, and dried under vacuum. The crude product was purified by column chromatography (silica, 3:2 dichloromethane/hexanes). During column packing, a portion of a poorly soluble yellow solid was isolated and found to be 2 (3.91 g, 6.60 mmol, 18%). The first band from the column afforded additional 2 as a yellow solid (0.650 g, 1.10 mmol, 21% overall yield). The second band gave 1 as a white solid (1.35 g, 2.63 mmol, 7%).

Data for 1: $^1$H NMR (400 MHz, CDCl$_3$) δ 8.88 (s, 1H), 8.77 (d, J=7.6 Hz, 1H), 8.72 (d, J=7.6 Hz, 1H), 4.16 (t, J=6.9 Hz, 2H), 4.14 (t, J=6.6 Hz, 2H), 1.71 (quint., J=7.1 Hz, 2H), 1.69 (quint., J=7.6 Hz, 2H), 1.45-1.24 (m, 12H), 0.87 (t, J=7.0 Hz, 6H). $^{13}$C{$^1$H} NMR (100 MHz, CDCl$_3$) δ 162.40, 161.79, 161.67, 160.99, 138.3, 131.62, 130.67, 128.62, 128.54, 126.79, 125.99, 125.92, 125.64, 123.85, 41.47, 41.09, 31.46, 31.44, 27.93, 27.88, 26.76, 26.67, 22.54, 22.50, 14.02 (one aliphatic resonance not observed, presumably due to overlap). HRMS (EI) m/z calcd for C$_{26}$H$_{29}$BrN$_2$O$_4$ (M$^+$), 512.1311. found, 512.1280. Anal. Calcd. For C$_{26}$H$_{29}$BrN$_2$O$_4$: C, 60.82; H, 5.69; N, 5.46. Found: C, 59.91; H, 5.60; N, 5.36.

Data for 2: $^1$H NMR (400 MHz, CDCl$_3$): δ 8.98 (s, 2H), 4.17 (t, J=7.8 Hz, 4H), 1.72 (quint., J=7.8 Hz, 4H), 1.49-1.20 (m, 12H), 0.88 (t, J=7.1 Hz, 6H). $^{13}$C{$^1$H} NMR (100 MHz, CDCl$_3$) δ 160.73, 139.06, 128.96, 128.32, 127.72, 125.34, 124.08, 41.61, 31.45, 27.84, 26.73, 22.54, 14.02. HRMS (EI) m/z calcd for C$_{26}$H$_{28}$Br$_2$N$_2$O$_4$ (M$^+$), 590.0416. found, 590.0394. Anal. Calcd. For C$_{26}$H$_{28}$Br$_2$N$_2$O$_4$: C, 52.72; H, 4.76; N, 4.73. Found: C, 52.71; H, 4.69; N, 4.70.

Example 2

Preparation of Compounds 3, 4 from a Mixture of 1, 2

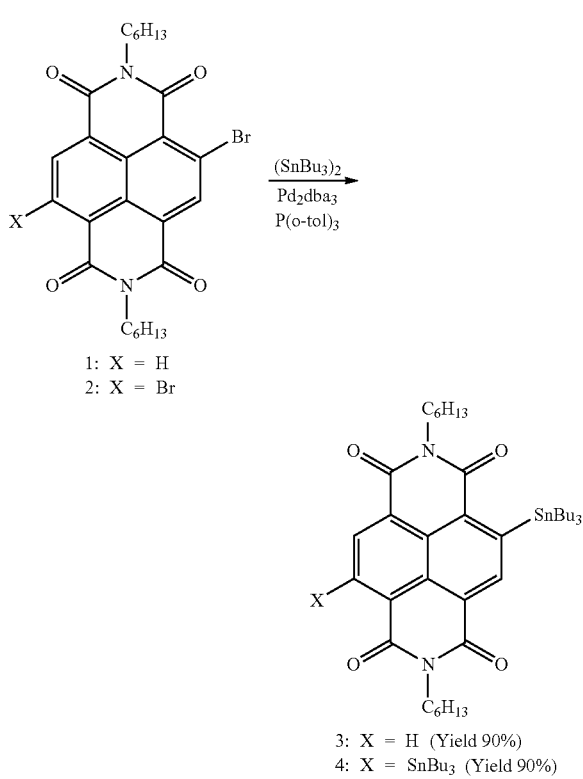

N,N'-di(n-hexyl)-2-tri-(n-butyl)stannylnaphthalene-1,4,5,8-bis(dicarboximide), 3, and N,N'-di(n-hexyl)-2,6-bis(tri(n-butyl)stannyl)naphthalene-1,4,5,8-bis(dicarboximide), 4, were obtained in good to moderate yields, respectively, according to the following general scheme. A mixture of the appropriate mono- or dibromo derivative, 1 or 2, and hexabutyltin (1 eq per bromo substituent) was heated in toluene in the presence of Pd$_2$dba$_3$ (0.05 eq per bromo) and P(o-tol)$_3$ (0.2 eq per bromo). Purification of the reaction products by silica gel chromatography and recrystallization from methanol afforded the mono- and distannyl derivatives as long yellow needles; these compounds were characterized by NMR spectroscopy, mass spectrometry, elemental analysis, and, in the case of 4, X-ray crystal structure.

In comparison, under identical conditions, the monobrominated perylene diimide (PDI) derivative undergoes homo-coupling to yield the bi-PDI product and the stannyl PDI intermediate could not be isolated.

The ability to isolate and thoroughly purify the distannyl derivative is important for applications in conjugated-polymer syntheses, where the ability to obtain high-molecular-weight material is critically dependent on precise control of monomer stoichiometry.

Example 3

Preparation of Compound 3 from Compound 1

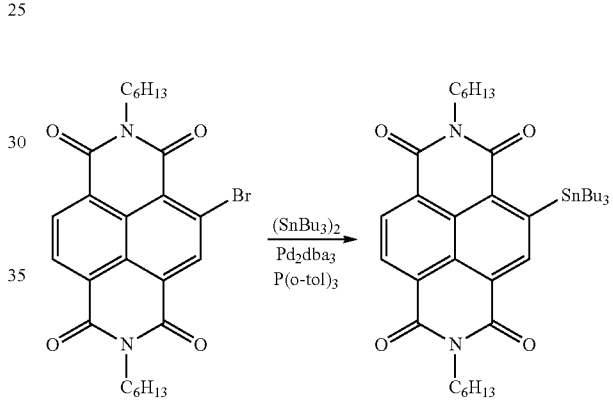

A solution of 1 (1.45 g, 2.82 mmol), 1,1,1,2,2,2-hexabutyldistannane (1.64 g, 2.82 mmol), and tri-o-tolylphosphine (0.172 g, 0.565 mmol) in dry toluene (30 mL) was deoxygenated with nitrogen for 5 min. Tris(dibenzylideneacetone)dipalladium (0.129 g, 0.141 mmol) was added and the reaction was heated to 90° C. for 24 h. After cooling, the reaction mixture was precipitated in methanol (100 mL), the solid was removed via filtration, and the solvent was removed under reduced pressure. The crude product was purified by column chromatography (silica, dichloromethane) to yield a yellow solid (1.53 g, 2.11 mmol, 75%). $^1$H NMR (400 MHz, CDCl$_3$) δ 8.94 (s, 1H), 8.70 (d, J=7.6 Hz, 1H), 8.67 (d, J=7.6 Hz, 1H), 4.18 (t, J=7.6 Hz, 2H), 4.16 (t, J=8.0 Hz, 2H), 1.75-1.64 (m, 4H), 1.55-1.45 (m, 6H), 1.40-1.23 (m, 18H), 1.19 (t, J=8.2 Hz, 6H), 0.90-0.80 (m, 15H). $^{13}$C{$^1$H} NMR (100 MHz, CDCl$_3$) δ 164.91, 163.62, 163.12, 163.04, 156.00, 138.65, 131.67, 130.24, 130.13, 126.84, 126.72, 126.70, 125.98, 123.64, 53.40, 41.00, 40.91, 31.50, 29.20, 28.25, 28.07, 28.02, 27.39, 26.76, 26.65, 22.54, 22.48, 17.27, 14.02, 13.69, 13.58, 11.58. HRMS (MALDI) m/z calcd for C$_{38}$H$_{56}$N$_2$O$_4$Sn (M+), 725.3340. found, 725.3325. Anal. Calcd. For C$_{38}$H$_{56}$N$_2$O$_4$Sn: C, 63.08; H, 7.80; N, 3.87. Found: C, 62.81; H, 7.99; N, 3.93.

Example 4

Preparation of Compound 4 from Compound 2

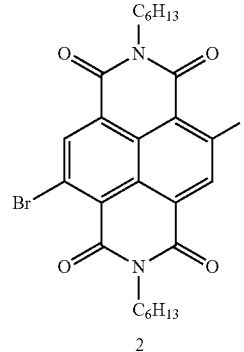

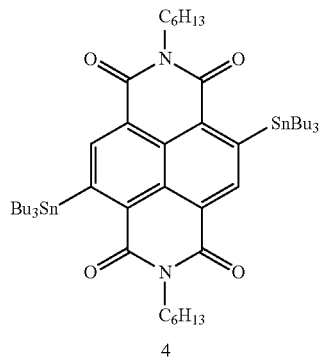

A solution of 2 (0.500 g, 0.844 mmol), 1,1,1,2,2,2-hexabutyldistannane (1.00 g, 1.73 mmol), and tri-o-tolylphosphine (0.051 g, 0.169 mmol) in dry toluene (10 mL) was deoxygenated with nitrogen for 5 min. Tris(dibenzylideneacetone)dipalladium (0.039 g, 0.042 mmol) was added and the reaction was heated to 90° C. for 24 h. Additional portions of tri-o-tolylphosphine (0.051 g, 0.169 mmol) and tris(dibenzylideneacetone)dipalladium (0.039 g, 0.042 mmol) were added and the reaction was stirred at 90° C. for an additional 2 d. After cooling, the reaction mixture was filtered through a plug of silica gel eluting with chloroform/hexanes (1:1) and the solvent was removed under reduced pressure. The crude product was recrystallized from methanol to yield a yellow solid (0.407 g, 0.402 mmol, 48%). $^1$H NMR (400 MHz, CDCl$_3$) δ 8.92 (s, 2H), 4.18 (t, J=7.4 Hz, 4H), 1.68 (quint., J=7.5 Hz, 4H), 1.53-1.46 (m, 12H), 1.45-1.36 (m, 4H), 1.35-1.25 (m, 20H), 1.23-1.09 (m, 12H), 0.90-0.80 (m, 24H). $^{13}$C{$^1$H} NMR (100 MHz, CDCl$_3$) δ 165.12, 163.82, 154.61, 138.04, 131.84, 126.90, 123.11, 40.92, 31.53, 29.22, 28.08, 27.39, 26.69, 22.49, 14.02, 13.69, 11.54. MS (MALDI) m/z 898.3 (M-(C$_4$H$_9$)$_2$$^2$). Anal. Calcd. For C$_{50}$H$_{82}$N$_5$O$_4$Sn$_2$: C, 59.31; H, 8.16; N, 2.77. Found: C, 59.30; H, 7.98; N, 2.83.

Example 5

Synthesis of 3-6 from NDA

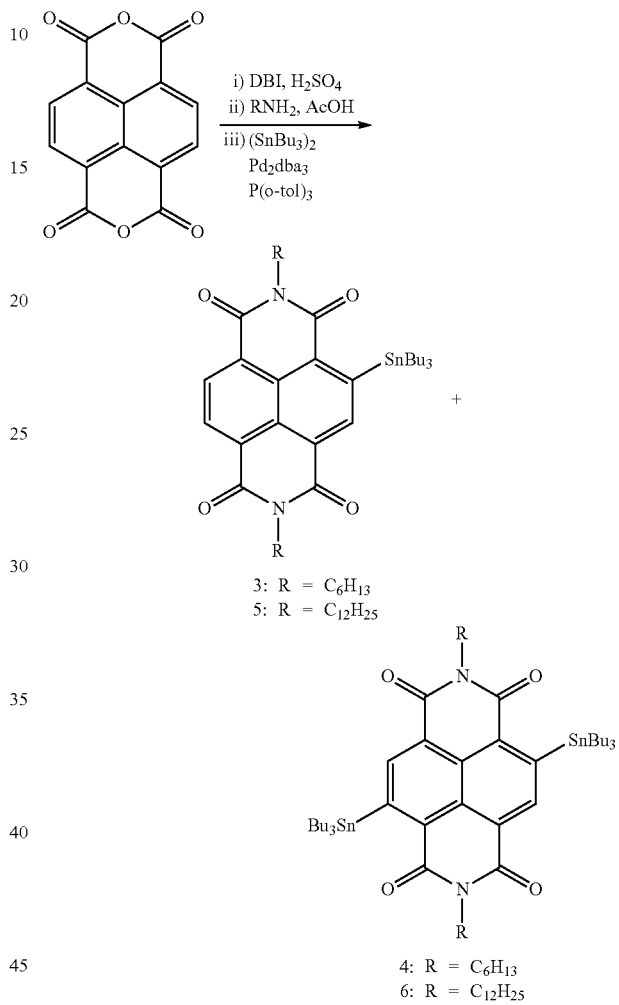

The different chromatographic behavior of 3 and 4 (3: R$_f$=0.3 on silica, eluting with 1:1 dichloromethane/hexanes; 4: R$_f$=0.3 on silica, eluting with 1:10 dichloromethane/hexanes) suggested the possibility of carrying out this reaction using a mixture of mono- and dibromo species obtained from bromination and imidization of NDA, only purifying at the final stage. This transformation can indeed be carried out without separation of the mono- and difunctionalized intermediates to give isolated yields of mono- and distannyl derivatives of ca. 20% and 5%, respectively (when using 1 eq. DBI as the brominating agent). The relative yields can be somewhat tuned with respect to the brominating agent and yields of ca. 10% were obtained for both mono- and distannyl derivatives using 2.1 eq. of DBI.

As shown, in addition to 3 and 4, their N,N'-bis(n-dodecyl) analogues 5 and 6 have also been obtained in similar isolated yield. The dodecyl group can improve solubility compared to, for example, a hexyl group.

The facile separation of the highly soluble mono- and distannyl NDI products via column chromatography is an attractive alternative to the more difficult purification of that of the mono- and dibromo-NDI intermediates, such as 1 and 2, which are both less soluble in common organic solvents and less well-differentiated in $R_f$ (0.4 and 0.3 for 1 and 2 on silica, eluting with dichloromethane). As such, a two-step isolation and purification of the brominated species followed by stannylation results in overall yields of ca. 9% and 2% for the mono- and distannyl NDI, respectively.

Example 6

Preparation of Compounds 3 and 4 from NDA

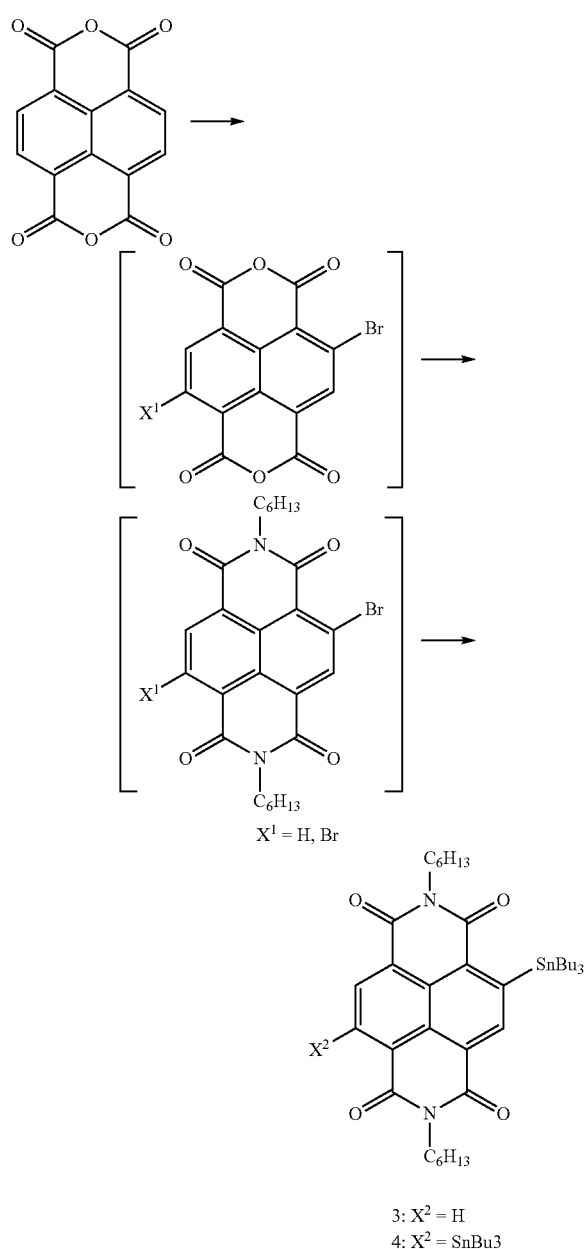

A solution of naphthalene-1,4,5,8-tetracarboxydianhydride (NDA) (5.00 g, 18.6 mmol) in concentrated sulfuric acid (180 mL) was heated to 55° C. In a separate flask, potassium dibromoisocyanurate (6.06 g, 18.6 mmol) was dissolved in concentrated sulfuric acid (90 mL) while stirring at room temperature for 1 h. Once dissolved, the solution was added to the reaction flask and the mixture was allowed to stir at 85° C. for 48 h. The mixture was poured into ice water (1 L) and allowed to stir for 2 h, while warming to room temperature. The resulting yellow precipitate was collected by filtration, washed with methanol, and dried under vacuum (4.51 g). The yellow solid was transferred to a flask with glacial acetic acid (100 mL) and n-hexylamine (7.2 g, 71.1 mmol). The reaction mixture was refluxed for 2 h, allowed to cool overnight, and poured into methanol (1 L). The resulting precipitate was collected by filtration, washed with methanol, and dried under vacuum (5.51 g). The orange solid was transferred to a dry Schlenk flask with 1,1,1,2,2,2-hexabutyldistannane (11.3 g, 19.5 mmol), tri-o-tolylphosphine (1.13 g, 3.71 mmol) and tris(dibenzylideneacetone)dipalladium (0.850 g, 0.930 mmol). The flask was pump-filled three times with nitrogen Anhydrous toluene (80 mL) was added and the reaction was heated to 100° C. for 18 h. After cooling, the reaction mixture was diluted with hexanes (100 mL) and filtered through a plug of silica gel eluting with hexanes. Dichloromethane/hexanes (1:1) was used to elute the first yellow band (impure 4). The second yellow band was collected using dichloromethane as an eluent and was evaporated to give 3 as a yellow solid (2.60 g, 3.59 mmol, 19% overall yield from NDA). The first fraction was further purified by column chromatography (silica gel, 10:1 hexanes/dichloromethane) to yield 4 a yellow solid (0.780 g, 0.770 mmol, 4% from NDA). $^1$H NMR data were consistent with those obtained for 3 and 4 synthesized from 1 and 2, respectively.

Example 7

Preparation of Compounds 5 and 6 from NDA

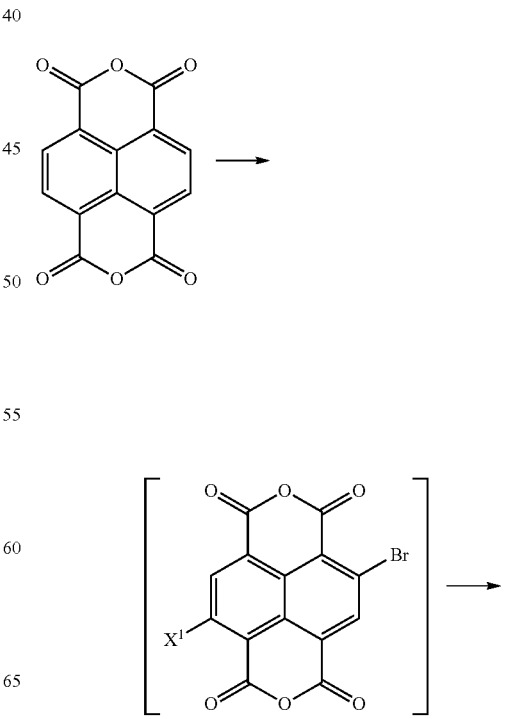

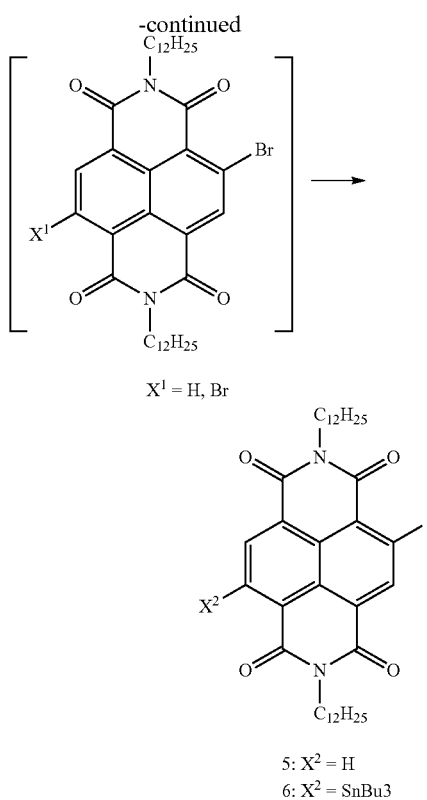

5: X² = H
6: X² = SnBu3

A solution of NDA (5.00 g, 18.6 mmol) in concentrated sulfuric acid (180 mL) was heated to 55° C. In a separate flask, potassium dibromoisocyanurate (6.06 g, 18.6 mmol) was dissolved in concentrated sulfuric acid (90 mL) while stirring at room temperature for 1 h. Once dissolved, the solution was added to the reaction flask and the mixture was allowed to stir at 85° C. for 48 h. The mixture was poured into ice water (1 L) and stirred for 2 h, while allowing to warm to room temperature. The resulting yellow precipitate was collected by filtration, washed with methanol, and dried under vacuum (8.33 g). The yellow solid was transferred to a flask with glacial acetic acid (190 mL) and n-dodecylamine (14.2 g, 76.4 mmol). The reaction mixture was refluxed for 2 h, allowed to cool overnight, and poured into methanol (1 L). The resulting precipitate was collected by filtration, washed with methanol, and dried under vacuum. The resultant orange solid (10.0 g) was transferred to a dry schlenk flask with 1,1,1,2,2,2-hexabutyldistannane (16.0 g, 27.6 mmol), tri-o-tolylphosphine (1.60 g, 5.26 mmol) and tris(dibenzylidene-acetone)dipalladium (1.20 g, 1.31 mmol). The flask was pump-filled three times with nitrogen Anhydrous toluene (60 mL) was added and the reaction was heated to 90° C. for 24 h. After cooling, the reaction mixture was diluted with hexanes, filtered through a plug of Celite, and the solvent was removed under reduced pressure. The crude product was purified by column chromatography (silica gel): the first band was eluted using hexanes/dichloromethane (10:1) and, on evaporation, gave a yellow oil (impure 6). The second band was eluted using hexanes/dichloromethane (1:1) and was evaporated to give 5 as a yellow solid (3.87 g, 4.34 mmol, 23% overall yield from NDA). The first yellow fraction was further purified by column chromatography (silica gel, 10:1 hexanes/toluene) to yield pure 6 as a yellow oil (1.25 g, 1.06 mmol, 6% overall yield from NDA).

Data for 5: $^1$H NMR (400 MHz, CDCl$_3$) δ 8.95 (s, 1H), 8.70 (d, J=7.6 Hz, 1H), 8.67 (d, J=7.7 Hz, 1H), 4.18 (m, 4H), 1.78-1.64 (m, 4H), 1.58-1.45 (m, 6H), 1.40-1.15 (m, 48H), 0.90-0.82 (m, 15H). $^{13}$C{$^1$H} NMR (100 MHz, CDCl$_3$) δ 164.90, 163.60, 163.09, 163.02, 155.98, 138.63, 131.65, 130.22, 130.12, 126.82, 126.71, 126.69, 125.96, 123.62, 40.98, 40.91, 31.89, 31.57, 28.61, 28.52, 29.48, 29.33, 29.20, 29.10, 28.12, 28.06, 27.39, 27.11, 26.99, 22.67, 14.09, 13.70, 11.57 (five aliphatic resonances not observed, presumably due to overlap). MS (MALDI) m/z 893.5 (7%, M$^+$), 835.4 (100%, M-(C$_4$H$_9$)). Anal. Calcd. For C$_{50}$H$_{80}$N$_2$O$_4$Sn: C, 67.33; H, 9.04; N, 3.14. Found: C, 67.40; H, 9.03; N, 3.13.

Data for 6: $^1$H NMR (300 MHz, CDCl$_3$) δ 8.93 (s, 2H), 4.19 (t, J=7.2 Hz, 4H), 1.71 (quint., J=7.3 Hz, 4H), 1.53-1.46 (m, 12H), 1.57-1.42 (m, 12H), 1.42-1.02 (m, 60H), 0.94-0.76 (m, 24H). $^{13}$C{$^1$H} NMR (75 MHz, CDCl$_3$) δ 165.11, 163.82, 154.60, 138.04, 131.84, 126.89, 123.10, 40.93, 31.90, 29.64, 29.62, 29.50, 29.38, 29.34, 29.23, 28.12, 27.41, 27.04, 22.67, 14.10, 13.72, 11.52 (one aliphatic resonance not observed, presumably due to overlap). MS (MALDI) m/z 1066.4 (M-(C$_4$H$_9$)$_2^{2+}$). Anal. Calcd. For C$_{62}$H$_{106}$N$_2$O$_4$Sn$_2$: C, 63.06; H, 9.05; N, 2.37. Found: C, 62.87; H, 9.09; N, 2.32.

What is claimed is:

1. A naphthalene diimide (NDI) compound comprising at least one stannyl substituent directly bonded to the naphthalene core of the NDI compound.

2. The compound of claim 1, which is represented by the structure:

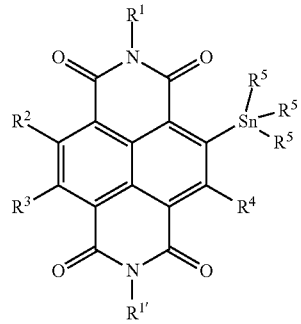

wherein
R$^1$ and R$^{1'}$ are independently selected from a C$_1$-C$_{30}$ normal, branched, or cyclic alkyl, aryl, heteroaryl, alkyl-aryl, or alkyl-heteroaryl group optionally substituted with one or more halide, cyano, alkyl, or alkoxy groups;

R$^2$, R$^3$, and R$^4$ are independently selected from hydrogen, halide, or a C$_1$-C$_{30}$ organic group independently selected from cyano, normal, branched, or cyclic alkyl, fluoroalkyl, aryl, heteroaryl, alkyl-aryl, and alkyl-heteroaryl groups, optionally substituted with one or more fluoro, cyano, alkyl, alkoxy groups, or one or more of R$^2$, R$^3$, and R$^4$ are optionally Sn(R$^5$)$_3$; and R$^5$ is an alkyl or aryl group.

3. The compound of claim 2, wherein
R$^2$, and R$^4$ are independently selected from hydrogen, fluoro and cyano; and
R$^3$ is independently selected from hydrogen, halide, or a C$_1$-C$_{30}$ organic group independently selected from cyano, normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups and Sn(R$^5$)$_3$ wherein R$^5$ is an alkyl or aryl group.

4. The compound of claim 1, which is a mono-stannyl NDI compound represented by the structure:

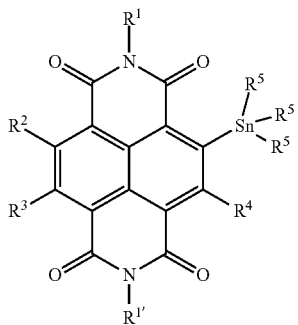

wherein
g) R$^1$ and R$^{1'}$ are independently selected from a C$_1$-C$_{30}$ normal, branched, or cyclic alkyl, aryl, heteroaryl, alkyl-aryl, or alkyl-heteroaryl group optionally substituted with one or more halide, cyano, alkyl, or alkoxy groups,
h) R$^2$, R$^3$, and R$^4$ are independently selected from hydrogen, halide, or a C$_1$-C$_{30}$ organic group independently selected from cyano, normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups; and
i) R$^5$ is an alkyl or aryl group.

5. The compound of claim 1, which is a bis-stannyl NDI compound represented by the structure:

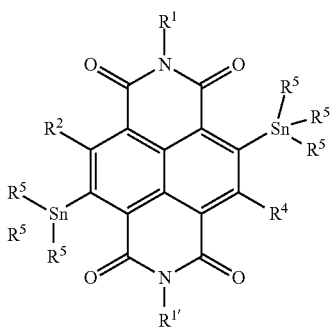

wherein
d) R$^1$ and R$^{1'}$ are independently selected from a C$_1$-C$_{30}$ normal, branched, or cyclic alkyl, aryl, heteroaryl, alkyl-aryl, or alkyl-heteroaryl group optionally substituted with one or more halide, cyano, alkyl, or alkoxy groups,
e) R$^2$ and R$^4$ are independently selected from hydrogen, halide, or a C$_1$-C$_{30}$ organic group independently selected from cyano, normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups; and
f) R$^5$ is an alkyl or aryl group.

6. A composition comprising at least one naphthalene diimide (NDI) compound as defined in claim 1.

7. A method comprising:
reacting at least one first naphthalene diimide (NDI) precursor compound with at least one tin reagent to form at least one first NDI reaction product compound comprising at least one stannyl substituent directly bonded to the naphthalene core of the NDI compound.

8. The method of claim 7, wherein the tin reagent is an organotin reagent.

9. The method of claim 7, wherein the tin reagent comprises one or more of a hexaalkyl ditin reagent, or a hexaaryl ditin reagent.

10. The method of claim 7, wherein the tin reagent is not a halogenated tin reagent.

11. The method of claim 7, wherein in the reacting step only one NDI precursor compound is reacted with the at least one tin reagent.

12. The method of claim 7, wherein the first NDI reaction product compound comprises one or two stannyl substituents.

13. The method of claim 7, wherein the first NDI reaction product comprises the structure:

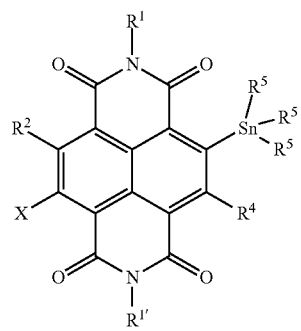

wherein X is H, R$^3$ or a stannyl substituent Sn(R$^5$)$_3$; wherein
R$^1$ and R$^{1'}$ are independently selected from a C$_1$-C$_{30}$ normal, branched, or cyclic alkyl, aryl, heteroaryl, alkyl-aryl, or alkyl-heteroaryl group optionally substituted with one or more halide, cyano, alkyl, or alkoxy groups;
R$^2$, R$^3$, and R$^4$ are independently selected from hydrogen, halide, or a C$_1$-C$_{30}$ organic group independently selected from cyano, normal, branched, or cyclic alkyl, fluoroalkyl, aryl, heteroaryl, alkyl-aryl, and alkyl-heteroaryl groups, optionally substituted with one or more fluoro, cyano, alkyl, alkoxy groups; and
R$^5$ is an alkyl or aryl group.

14. The method of claim 7, wherein the first NDI reaction product comprises a mixture of the following structures:

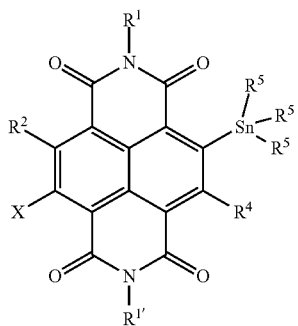

wherein X is H or $R^3$; and:

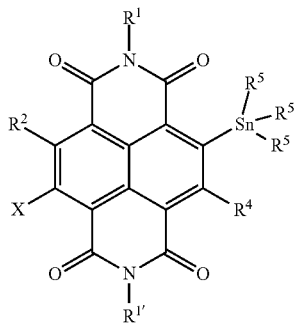

wherein X is $Sn(R^5)_3$,
wherein
  $R^1$ and $R^{1'}$ are independently selected from a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups;
  $R^2$, $R^3$, and $R^4$ are independently selected from hydrogen, halide, or a $C_1$-$C_{30}$ organic group independently selected from cyano, normal, branched, or cyclic alkyl, fluoroalkyl, aryl, heteroaryl, alkyl-aryl, and alkyl-heteroaryl groups, optionally substituted with one or more fluoro, cyano, alkyl, alkoxy groups; and
  $R^5$ is an alkyl or aryl group.

15. The method of claim 7, wherein the reacting step is carried out in the presence of at least one metal catalyst.

16. The method of claim 7 further comprising separating the stannyl NDI reaction products via chromatography.

17. The method of claim 7 wherein the at least one first naphthalene diimide (NDI) precursor compound is a monomeric naphthalene diimide precursor compound represented by the structure:

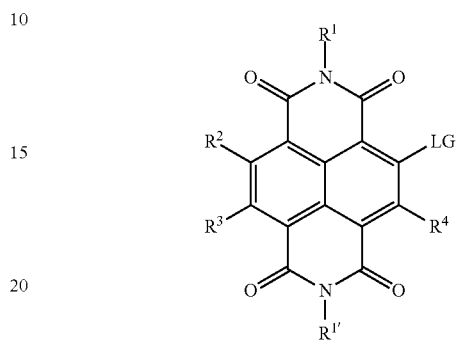

wherein LG is a halogen;
  $R^1$ and $R^{1'}$ are independently selected from a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups;
  $R^2$, $R^3$, and $R^4$ are independently selected from hydrogen, halide, or a $C_1$-$C_{30}$ organic group independently selected from cyano, normal, branched, or cyclic alkyl, fluoroalkyl, aryl, heteroaryl, alkyl-aryl, and alkyl-heteroaryl groups, optionally substituted with one or more fluoro, cyano, alkyl, alkoxy groups;
  and wherein the at least one tin reagent is a compound having the structure $(R^5)_3Sn—Sn(R^5)_3$, wherein
    $R^5$ is an alkyl or aryl group and wherein the reacting step is carried out in the presence of a catalyst.

18. A method for making an oligomer or polymer comprising reacting at least one naphthalene diimide (NDI) compound as defined in claim 1 with at least one bromide-substituted heteroaryl compound in the presence of a catalyst, thereby forming the oligomer or polymer.

19. A device comprising the oligomer or polymer of claim 18, wherein the device is an OLED, OPV, OFET, or sensing device.

* * * * *